(12) United States Patent
Badiei et al.

(10) Patent No.: US 8,873,053 B2
(45) Date of Patent: Oct. 28, 2014

(54) METHOD AND SYSTEM FOR GAS MEASUREMENTS IN A COMBUSTION CHAMBER

(75) Inventors: Shahriar Badiei, Gävle (SE); Magnus Berg, Trosa (SE)

(73) Assignee: Vattenfall AB, Stockholm (SE)

( * ) Notice: Subject to any disclaimer, the term of this patent is extended or adjusted under 35 U.S.C. 154(b) by 0 days.

(21) Appl. No.: 14/003,477

(22) PCT Filed: Mar. 7, 2012

(86) PCT No.: PCT/SE2012/050254
§ 371 (c)(1),
(2), (4) Date: Oct. 3, 2013

(87) PCT Pub. No.: WO2012/121654
PCT Pub. Date: Sep. 13, 2012

(65) Prior Publication Data
US 2014/0016130 A1  Jan. 16, 2014

(30) Foreign Application Priority Data
Mar. 8, 2011 (SE) .................................... 1150205

(51) Int. Cl.
| | | |
|---|---|---|
| G01N 21/00 | (2006.01) | |
| G01N 21/53 | (2006.01) | |
| G01N 21/51 | (2006.01) | |
| G01N 21/65 | (2006.01) | |
| G01K 11/12 | (2006.01) | |
| F23N 5/02 | (2006.01) | |
| F23N 5/08 | (2006.01) | |
| G01N 21/47 | (2006.01) | |
| G01K 11/32 | (2006.01) | |

(52) U.S. Cl.
CPC ........ G01N 21/51 (2013.01); *G01N 2021/4709* (2013.01); G01N 21/53 (2013.01); G01N 21/65 (2013.01); *G01N 2201/0697* (2013.01); *G01K 2011/322* (2013.01); G01K 11/125 (2013.01); F23N 5/02 (2013.01); F23N 5/082 (2013.01)
USPC ............................ 356/342; 356/337; 356/338

(58) Field of Classification Search
CPC ..... G01N 21/53; G01N 21/718; G01N 21/71; G01N 2021/4709; G01N 2021/1793; G01N 2021/3137; G01N 2021/3166; G01N 2021/3513; G01N 2021/4707; G01N 2021/4728; G01N 21/31; G01N 21/3504; G01N 21/658
See application file for complete search history.

(56) References Cited

U.S. PATENT DOCUMENTS

| | | |
|---|---|---|
| 3,625,613 A | 12/1971 | Abell et al. |
| 6,542,831 B1 | 4/2003 | Moosmuller et al. |
| 2010/0194574 A1* | 8/2010 | Monk et al. .................. 340/627 |

FOREIGN PATENT DOCUMENTS

| | | |
|---|---|---|
| DE | 44 16 270 A1 | 11/1995 |
| EP | 0 837 316 A2 | 4/1998 |

(Continued)

*Primary Examiner* — Michael P Stafira
(74) *Attorney, Agent, or Firm* — Birch, Stewart, Kolasch & Birch, LLP (57) ABSTRACT

The present invention relates to a method for determining at least one gas condition at a location in a combustion chamber of a power plant or a combined heat and power plant by means of a laser pulse. The method comprises emitting (S1) the laser pulse into the chamber, determining (S2) a first point of time at which the laser pulse is emitted into the chamber, detecting (S3) laser light backscattered by gas molecules at the location in the chamber, determining (S4) a second point of time at which the laser light backscattered by the gas molecules is detected, determining (S5) the location based on the first point of time, the second point of time, and a pulse length of the laser pulse, and determining (S5) the at least one gas condition at the location based on at least one characteristic of the backscattered laser light detected at the second point of time. A gas measurement system and a combustion system are also presented herein.

20 Claims, 5 Drawing Sheets

(56) References Cited

FOREIGN PATENT DOCUMENTS

| | | |
|---|---|---|
| JP | 2004-069251 A | 3/2004 |
| WO | WO 95/00833 A1 | 1/1995 |
| WO | WO 2004/090496 A2 | 10/2004 |
| WO | WO 2009/091437 A1 | 7/2009 |

* cited by examiner

METHOD AND SYSTEM FOR GAS MEASUREMENTS IN A COMBUSTION CHAMBER

TECHNICAL FIELD

The present invention generally relates to gas measurement and in particular to a method and arrangement for determining a gas condition and its location in a chamber.

BACKGROUND

Generally, it may be desirable to know properties of a gas flowing in a combustion system, such as in a boiler for steam generation in a power plant. In particular, it may be desirable to determine for instance the temperature of the gas in various locations in the combustion system. By determining the local temperature of the gas, it may be possible to control the gas flow or fuel distribution such that the gas temperature is optimally distributed as it flows through the combustion system. Thereby optimal combustion and minimal wear in the combustion system may be achieved.

One way to measure temperatures in a combustion system is by utilizing thermocouples mounted on the inside of the combustion chamber. However, in this way only the local gas temperature in one position will be measured for each thermocouple and the measured temperature is affected by radiation and therefore often deviates from the true gas temperature.

In order to obtain measurements of the gas temperatures in a cross-section of the gas flow in the boiler, acoustic methods have previously been utilized. To this end acoustic waves can be transmitted into the combustion system, whereby the temperature of the gas may be determined as a function of the time it takes for the acoustic wave to travel in the gas. This is due to the propagation speed of an acoustic wave being a function of the temperature of the gas. A plurality of transmitters may be distributed on the internal boiler wall in order to be able to obtain a two-dimensional image of the temperature distribution. However, high computational resources are needed for processing the measurements to be able to generate the two-dimensional image of the temperature distribution. For instance, it may be necessary to utilize interpolation in portions of the plane where no measurements have been carried out to be able to generate the temperature distribution image.

The concentration of individual gas molecules of a gas specie is another property of a gas that is desirable to know in a combustion system. By determining the gas concentration, the gas flow may be controlled so as to provide optimal concentration of the gas, whereby higher efficiency in regards of combustion in the combustion system may be achieved. More specifically, oxygen ($O_2$) and other combustion gases such as carbon monoxide (CO) may be mixed uniformly such that the combustion becomes more efficient. Furthermore, the formation of $NO_x$-gases is also reduced.

Suction pyrometric methods are known for determining a gas temperature in a combustion chamber. Suction pyrometry involves withdrawing gas from the combustion chamber, the gas passing a shielded thermocouple such that radiation effects are minimized and the true gas temperature is measured. With this technique temperatures up to 1100° C. may typically be measured. With more expensive materials, temperatures up to approximately 1600° C. can be measured. The extracted gas can thereafter be used also for determining the concentration of various gases in the combustion chamber. By positioning the probe at various locations in the combustion chamber, a spatial distribution of the concentration and temperature may be obtained. However, suction pyrometry does not provide for an efficient method to determine the spatial distribution of the concentration or temperature of the gas in the combustion system. In particular, it does not provide a real-time tool for determining the spatial distribution of the gas concentration and/or gas temperature.

SUMMARY

In view of the above, there is a need to provide an improved method and system for determining a spatial temperature distribution and/or concentration of a gas in a chamber of e.g. a combustion system.

Hence, a general object of the invention is to provide a method and a gas measurement arrangement for determining a gas condition and its location in a chamber.

In a first aspect of the present invention there is provided a method for determining at least one gas condition at a location in a combustion chamber of a power plant or a combined heat and power plant by means of a laser pulse, the method comprising: emitting the laser pulse into the chamber; determining a first point of time at which the laser pulse is emitted into the chamber; detecting laser light backscattered by gas molecules at the location in the chamber; determining a second point of time at which the laser light backscattered by the gas molecules is detected; determining the location based on the first point of time, the second point of time, and a pulse length of the laser pulse; and determining the at least one gas condition at the location based on at least one characteristic of the backscattered laser light detected at the second point of time.

By utilizing laser light, the measurement system will not be temperature dependent in the sense that the measurement system of the present invention are not sensitive to temperatures as they typically are located outside the chamber. Furthermore, the spatial pulse length of the laser pulse, which for instance may be 0.2-0.3 meter, provides for a very high spatial resolution in determining the location of the group of gas molecules in the chamber. Moreover, measurements providing a spatial distribution of the gas condition may be carried out in real-time.

A gas condition is herein defined as a condition of a gas. A gas condition may for instance be a (local) temperature of the gas in the chamber, a (local) concentration of the gas in the chamber.

One embodiment may comprise determining the at least one characteristic.

The characteristic of the backscattered laser light should be construed in the broad sense herein. In particular a characteristic of laser light could for instance mean spectral characteristics, such as energy and wavelength of the laser light. Other examples of characteristics of laser light could be the intensity of the light, or an amount of photons contained in the detected backscattered light.

The determining of the at least one characteristic may involve determining an amount of the backscattered laser light. Thereby, the concentration of the gas may be determined as a function of the determined amount of backscattered light.

By determining the concentration of the gas in a specific location in the chamber, it may be possible to control the gas distribution or gas flow so as to obtain a uniform gas concentration in the chamber. Thereby, if the chamber is a combustion chamber or part of a boiler, the combustion may be more efficient, thus resulting in a higher level of combustion. In power plant applications this means that power generation becomes more efficient while reducing costs associated with the power generation, as less fuel is needed to obtain similar effects over time. Moreover, the generation of $NO_x$-gases may be reduced.

The determining the at least one characteristic may involve determining a spectral property of the backscattered laser light. Thereby, the temperature of the gas may be determined. Thereby uniform temperature distribution may be obtainable by controlling the gas flow according to the determined temperature distribution.

The detected backscattered laser light may be Rayleigh scattered laser light.

The detected backscattered laser light may be Raman scattered laser light. Raman scattering provides Stokes and anti-Stokes scattering; both types of scattering resulting in an energy difference between the energy of the photons of the laser pulse prior to being scattered by gas molecules and the backscattered laser light. By measuring this difference, the temperature of the gas in the chamber may be determined. Raman scattering also provides information for determining the concentration of the gas by means of the amount of detected Raman scattered light.

One embodiment may further comprise defining a wavelength of the laser pulse. By defining the wavelength of the laser pulse, a temperature determination of the gas at the location where the light was backscattered may be performed based on Raman scattering.

One embodiment may comprise detecting additional backscattered laser light by gas molecules moving towards the location from the laser pulse propagating in a second plane different than a first plane in which the laser pulse initially propagated in when emitted into the chamber.

One embodiment may comprise determining a concentration of the gas molecules, and based on the determining of the at least one gas condition at the location in the first plane, and the determined concentration of the gas molecules in the second plane, determining a flow rate of the gas at the location in the first plane.

According to a second aspect of the present invention, there is provided a gas measurement arrangement for determining at least one gas condition at a location in a combustion chamber of a power plant or a combined heat and power plant, the gas measurement system comprising: a laser device arranged to emit a laser pulse having a predetermined length into the chamber; a scattering detector arranged to detect light backscattered by gas molecules at the location in the chamber; and a processing arrangement adapted to: determine a first point of time at which the laser pulse is emitted into the chamber, determine a second point of time at which the backscattered laser light is detected by the scattering detector, determine the location of the gas condition based on the first point of time, the second point of time and a pulse length of the laser pulse, and determine the at least one gas condition at the location based on at least one characteristic of the backscattered light detected at the second point of time.

The processing arrangement may be arranged to determine an amount of the backscattered laser light to thereby determine a concentration of the gas at the location of the at least one gas condition.

The processing arrangement may be arranged to determine a temperature at the location of the gas condition based on spectral characteristics of the backscattered laser light.

In a third aspect of the present invention there is provided a combustion system comprising: a gas measurement arrangement as disclosed above, a combustion chamber adapted to accommodate gas, the chamber having a enclosing wall with an opening arranged to allow a laser pulse from the laser device to be emitted into the combustion chamber.

One embodiment may comprise a window unit arranged in the opening of the chamber, which laser pulse input unit is arranged to allow a laser pulse from the laser device to be emitted into the chamber, the window unit being arranged to be fed by a gas external to the chamber, which gas external to the chamber has a higher pressure than the gas in the chamber.

All of the above aspects of the present invention generally present the same or similar advantages, as would be apparent to the skilled person.

Additional features and advantages will be disclosed in the following.

BRIEF DESCRIPTION OF THE DRAWINGS

The invention and the advantages thereof will now be described by way of non-limiting examples, with reference to the accompanying drawings of which.

DETAILED DESCRIPTION

The present invention is generally based on the realization of the inventors that light may be used for determining a condition of a gas and the location of the condition in a chamber or a duct which accommodates the gas, and in which the gas may flow.

In particular, the inventors have realized that Light Detection and Ranging (LIDAR) techniques may be utilized for determining a gas condition and the location of said gas condition in a chamber.

LIDAR techniques may in general be used to measure physical or chemical properties of gases or aerosols. LIDAR measurements usually employ laser light due to its coherence and narrow beam.

LIDAR techniques normally utilize a predefined laser light pulse to enable ranging that is positioning the pulse by determining its traveling time and the traveling time of the (back) scattered light. The pulse length in turn determines the minimum spatial resolution.

When laser light collides with molecules, part of the laser light is backscattered. The backscattered light may for instance be Rayleigh scattered light or Raman scattered light.

Figure 1A:
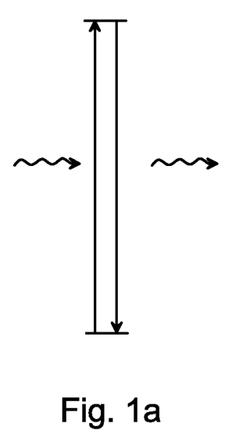
FIGS. 1a-c shows elastic and inelastic backscattering of photons.
Figure 1B:
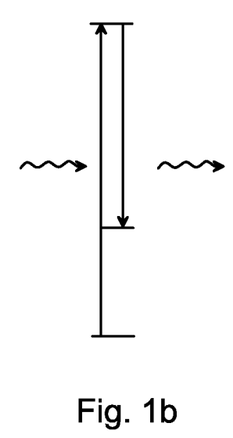
Figure 1C:
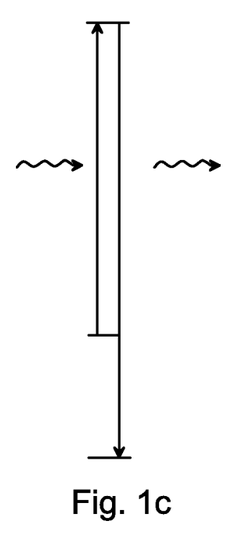

The concept of Raman scattering and Rayleigh scattering will now be described in more detail with reference to FIGS. 1a-c.

Rayleigh scattering involves so-called elastic scattering in the sense that backscattered photons have the same energy as prior to the occurrence of the photon-molecule collision. In this case a laser photon collides with a gas molecule, thereby exciting the molecule. The excited molecule then emits a photon with the same energy as that photon had which excited the molecule. This phenomenon is shown in FIG. 1a.

Raman scattering involves so-called inelastic scattering in the sense that the emitted photon will have different energy compared to the energy of the laser light photon prior to the collision with the molecule. Such an inelastic scattering may be in the form of Stokes scattering or Anti-Stokes scattering.

Stokes scattering means that the backscattered photon emitted after collision will have lower energy than the laser photon which exited the molecule. Thus, the wavelength of the backscattered light will be longer than prior to the collision. Stokes scattering of a photon is schematically shown in FIG. 1b.

Anti-Stokes scattering means that the backscattered photon will have higher energy than the laser photon prior to the collision with the molecule. Thus, the wavelength of the backscattered light will be shorter than prior to the collision. Anti-Stokes scattering of a photon is schematically shown in FIG. 1c.

Figure 2:
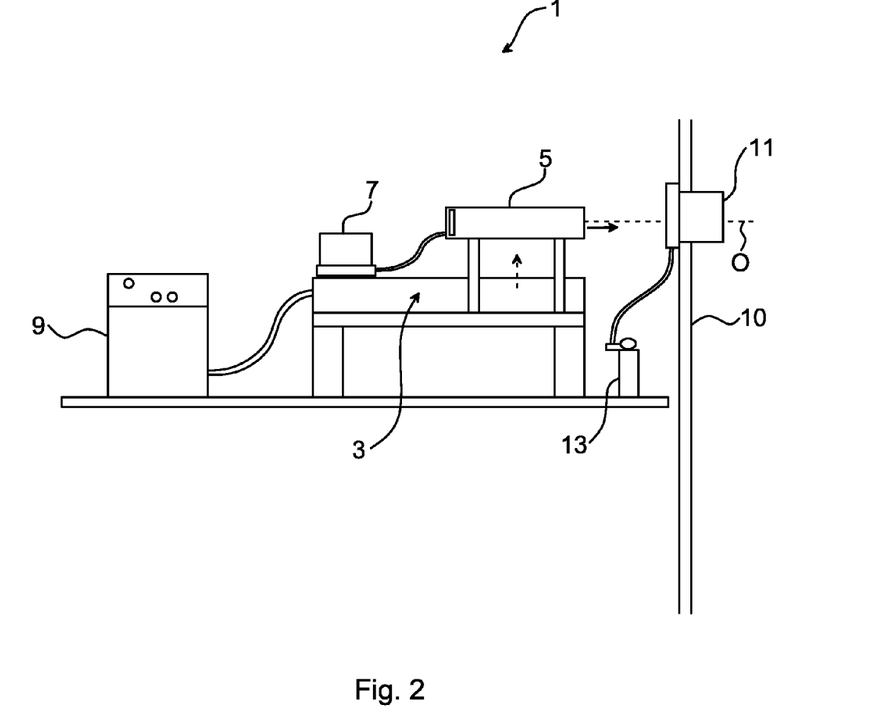
FIG. 2 shows an example of a gas measurement arrangement.

FIG. 2 shows an example of a gas measurement arrangement 1 according to the present invention. The gas measurement arrangement 1 may generally be utilized for determining gas conditions and their respective location in a chamber. Such a chamber may be any kind of chamber suitable for accommodating a gas and for allowing a gas to flow through the chamber. The chamber may for instance be a combustion chamber of a power plant, a heat plant or a combined heat and power plant. In the following, a chamber will generally be exemplified by a portion of a boiler for steam generation in a power plant.

The exemplified gas measurement system 1 utilizes optical methods for determining a gas condition and its location in a chamber. In particular, the exemplified gas measurement system 1 advantageously utilizes LIDAR techniques for determining a condition in a gas and the location of the gas condition in the chamber in which the gas is accommodated.

The gas measurement system 1 comprises a laser device 3, a scattering detector 5, a processing arrangement 7, a power supply 9 for providing power to the laser device 3, a window unit 11 and a pump unit 13 connected to the window unit 11.

The laser device 3 may in one embodiment be a laser which is capable of emitting laser pulses. The laser device 3 may for instance be a Nd:YAG laser, an excimer pumped dye laser or any other equivalent laser device type. The wavelength of a laser pulse may for example be between 266 to 1064 nm. The spot size of the laser pulse may be between e.g. 3 to 15 mm. The duration of a pulse may e.g. be in the range $30 \times 10^{-12}$ seconds to $10 \times 10^{-9}$ seconds, providing a spatial pulse length in the range 0.009 m to 3 m. The pulse length determines the spatial resolution of the measurements. The time duration and spatial length of the pulse is generally dependent of the specific application. The pulse repetition rate of the laser can for instance be 10 Hz to 1000 Hz with any pulse intensity.

The window unit 11, which may be arranged in an opening of the combustion chamber wall 10 provides for a window into the chamber. The laser device 3 is arranged such that a laser pulse emitted by the laser device 3 can enter the chamber through the window unit 11. The window unit 11 is fed with gas from the pump unit 13. The pump unit 13 may in one embodiment be a gas cylinder. The gas, sometimes referred to as a purge gas, provided by the pump unit 13 to the window unit 11 typically has a higher pressure than the gas which flows in the chamber. Thereby the window unit 11 is protected by the purge gas. By utilizing the window unit 11, laser pulses may be provided into the chamber and backscattered light may be detected by the scattering detector 5 while generally always providing a clean optical interface between the chamber and the exterior of the chamber.

The chamber may for instance be a furnace, wherein the chamber wall is a furnace wall.

In the embodiment shown in FIG. 2, the laser device 3 is arranged such that the laser device 3 emits laser pulses in a vertical direction towards an underside of the scattering detector 5. This arrangement may for instance be realized by means of a mirror arrangement in front of the laser device 3. The scattering detector 5 comprises a mirror arrangement (not shown) for directing a laser pulse towards the window unit 11 and thus into the chamber. Thereby it is known that backscattered light which is detected by the scattering detector 5 has been backscattered by molecules or atoms in the same plane as an optical axis O along which the laser light propagates.

In one embodiment, the scattering detector 5 may comprise a telescope configuration and a dedicated detector system. The scattering detector 5 may comprise one or more radiation sensitive elements, such as Photomultiplier Tubes (PMT). PMTs are able to convert collected radiation to electric signals that may be further digitally processed.

Embodiments which depend on Raman scattering typically have a filter arranged in the scattering detector for filtering Rayleigh scattered light from the Raman scattered light. Thereby detection and processing may be concentrated to Raman scattered light. In such embodiments, two or more PMTs may be connected in series. Each PMT may then be arranged to detect one of Anti-Stokes and Stokes scattered light. Thus, a first PMT may for instance be arranged to detect Anti-Stokes scattering from a gas specie and a second PMT may be arranged to detect Stokes scattering from the same gas specie. The signal quotient between the number of Stokes and Anti-Stokes scattered photons provides for determining the temperature in the gas in the chamber at the location where these photons were backscattered in the chamber. The spatial pulse length determines the spatial resolution of the determined location.

The scattering detector 5 may be calibrated to take into account the gas provided by the pump unit 13 to the window unit 11 in order to eliminate measurement errors due to backscattering provided by that gas. Alternatively, the processing arrangement 7 may be calibrated to take into account the gas provided by the pump unit 13 to the window unit 11 in order to eliminate measurement errors due to backscattering provided by that gas.

The processing arrangement 7 is operatively coupled to the scattering detector 5. The processing arrangement 7 may be an integrated unit which processes data received from the scattering unit 5. Alternatively, the processing arrangement may comprise several units together forming the processing arrangement.

Figure 3A:
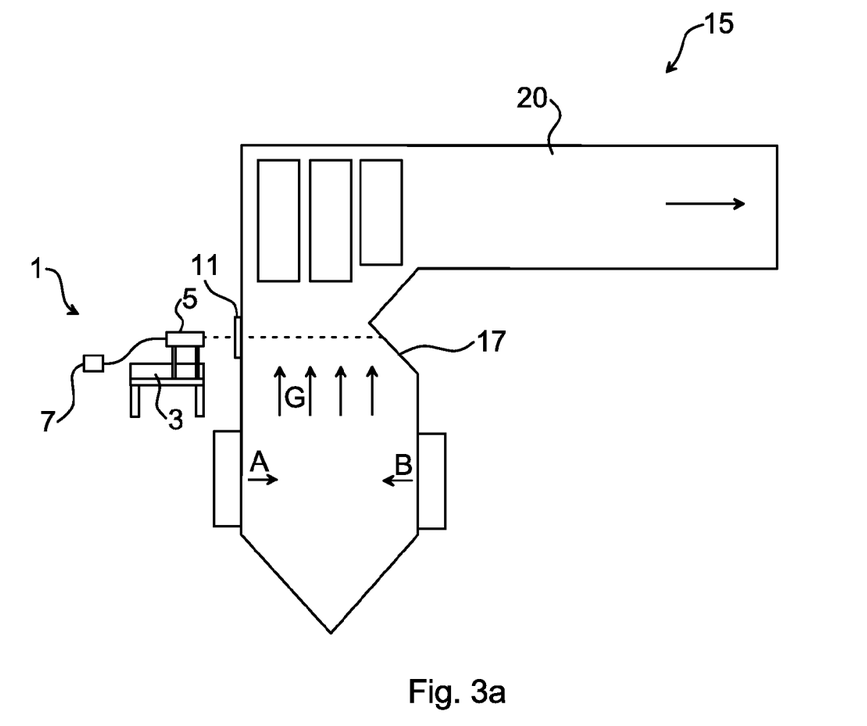
FIG. 3 shows a first example of gas measurement by means of the gas measurement arrangement in FIG. 2.

With reference to FIG. 3a, a first example of determining a condition in a gas and its location in a chamber will now be described in more detail.

FIG. 3a shows a schematic side view of a combustion system 15 comprising a combustion chamber 17, such as a furnace, and the gas measurement arrangement 1. For reasons of clarity, not all features of the gas measurement system 1 have been illustrated in FIG. 3a.

Air or oxygen is provided to the combustion chamber 17 as shown by arrow A. Furthermore, fuel such as oil, coal or natural gas, is provided to the combustion chamber 17 as shown by arrow B. The mixtures are ignited and combustion takes place in the zone where fuel and oxygen/air is provided. By means of the gas measurement arrangement 1 it is possible to determine the spatial distribution of the temperature and the concentration of a gas G which flows through the combustion system 15, which gas G is a result of the burning of air or oxygen and fuel in the combustion chamber 17.

In the present example the gas G flows in a vertical direction upwards in the combustion system 15. It is however to be noted for the purposes of the present invention, the gas may in general flow in any direction depending on the orientation of the combustion system.

The gas G flows through the combustion chamber through a flue gas duct 20 towards a boiler region where it may heat a fluid such as water for steam generation. The gas G is typically a mixture of several gases such as nitrogen, carbon dioxide, oxygen, carbon monoxide, sulphur compounds ($SO_x$) and $NO_x$-gases.

Figure 5:
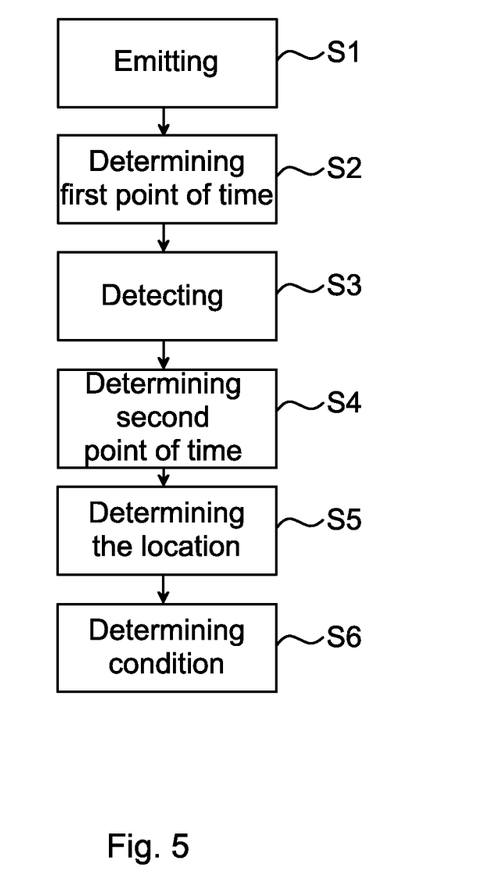
FIG. 5 shows a flowchart of a method of determining a condition and its location in a gas.

In order to determine a spatial distribution of a condition in the gas G in a cross-section at the optical axis O, a laser pulse is emitted by the laser device 3 and provided into the combustion chamber 17 in a step S1, as also shown in FIG. 5. A laser pulse may for instance be provided into the combustion chamber 17 at a rate of 10 Hz or 500 Hz.

The basic principles of backscattering will now be described in more detail with reference to FIG. 3b.

A laser pulse P which is emitted into the combustion chamber 17 via the window unit 11 propagates through the combustion chamber 17. The laser pulse P propagates between inner walls 17-1 of the combustion chamber 17. The laser pulse P has a length l determined by the pulse duration.

The gas G which flows through the combustion chamber G comprises a plurality of molecules, such as molecules M-1, M-2 and M-n. In the following, the molecules M-1, M-2 and M-n will be exemplified by oxygen molecules. It is to be noted that in general, a great plurality of molecules is distributed in each arbitrarily selected volume unit in the combustion chamber. However, for the sake of simplicity, the present example will be based on three molecules.

The gas G is generally a non-uniform mixture of several molecule types, as has been described above. The gas G may also have different temperature in different portions of the gas G.

As the laser pulse P propagates through the gas G in the combustion chamber 17, photons will be backscattered by molecules in the gas G. This is illustrated in the present example by photons 19-1, 19-2 and 19-n which are backscattered by the molecules M-1, M-2 and M-n, respectively. The molecules M-1, M-2 and M-n are located in close proximity at a distance d from the inner wall 17-1 from which the laser pulse P has been emitted into the combustion chamber 17. The processing arrangement 7 has in a step S2 received data pertaining to a first point in time when the laser pulse P entered the combustion chamber 17.

For the sake of example, it is assumed that photon 19-1 is backscattered as Anti-Stokes scattering, meaning that the photon 19-1 will have a shorter wavelength than the wavelength of the laser pulse P. Furthermore, it is assumed that photon 19-2 is backscattered as Stokes scattering, meaning that the photon 19-2 will have a longer wavelength than the wavelength of the laser pulse P. Moreover, it is assumed that photon 19-n is backscattered as Rayleigh scattering.

The backscattered photons 19-1, 19-2 and 19-n are detected in a step S3 by means of the scattering detector 5 after the photons 19-1, 19-2 and 19-n have exited the combustion chamber 17 through the window unit 11.

The Rayleigh scattered photon 19-n is filtered by means of a filter. The Anti-Stokes scattered photon 19-1 and the Stokes scattered photon 19-2 are detected by a respective PMT in the scattering detector 5.

The processing arrangement 7 receives data from the scattering detector 5 regarding the number of Stokes scattered photons detected and the number of Anti-Stokes scattered photons detected. Furthermore, a second point of time, namely the time when the detection of the photons occur is also registered in a step S4. The change in wavelength of the backscattered photons 19-1 and 19-2 is utilized by the processing arrangement 7 to determine the type of the molecules M-1 and M-2. By means of the amount of detected backscattered molecules from the distance d, the processing arrangement 7 can determine the concentration of oxygen at distance d in a step S6. The location of the molecules M-1 and M-2 is determined by the distance d and the spatial resolution is determined by the predetermined pulse length l of the laser pulse P in a step S5. Thereby the location of the molecules M-1 and M-2 can be determined to be at a distance d with a spatial resolution of length l.

The temperature of the molecules M-1 and M-2 may be determined based on a quotient between the backscattered Raman photons 19-1 and 19-2. In general, the temperature of the gas G at a specific location may be determined based on the quotient of the total amount of backscattered Stokes and Anti-Stokes photons.

It is to be noted that instead of Raman scattering, Rayleigh scattering may be used to determine the spatial temperature distribution of the gas in the combustion chamber.

Figure 4:
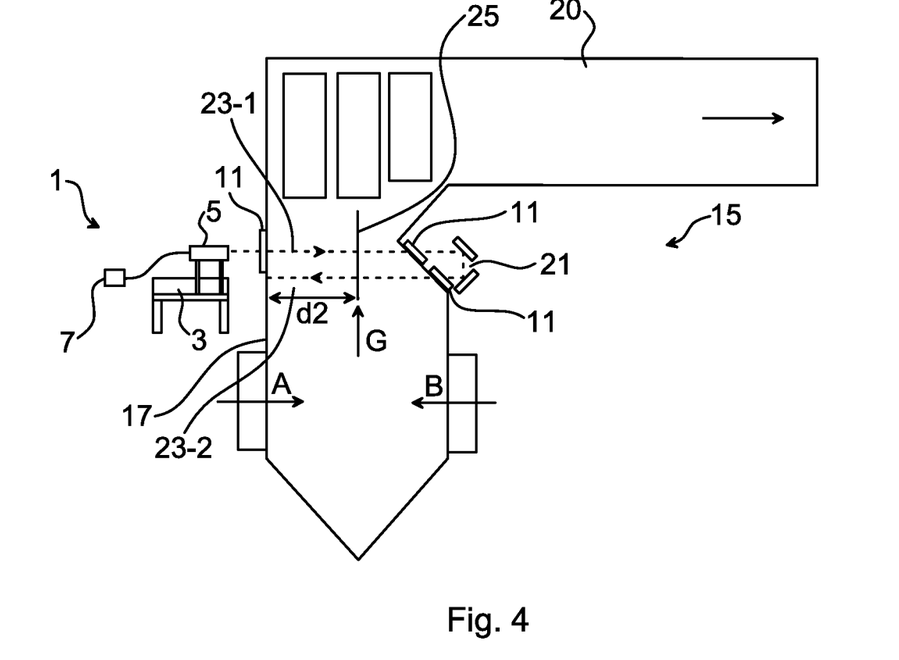
FIG. 4 shows a second example of a gas measurement by means of the gas measurement arrangement in FIG. 2.

With reference to FIG. 4, a further application of the present invention is shown. In the application shown in FIG. 4a, also a spatial distribution of the flow rate of the gas G can be determined. Thereby, the mass flow may also be determined.

The combustion system 15 shown in FIG. 4 is similar to that of FIG. 3a. In the example of FIG. 4, the gas measurement assembly 1 further comprises a mirror arrangement 21 arranged on an opposite side of the combustion chamber 17 with respect to the laser device 3 and the scattering detector 5.

In the present example, the mirror arrangement 21 is arranged externally to the combustion chamber 17. Window units 11 are therefore arranged in the combustion chamber wall opposite the wall where the scattering detector 5 is arranged. Thereby laser pulses may exit the combustion chamber 17 for being redirected by the mirror arrangement 21 outside the combustion chamber 17 and led back into the combustion chamber via a window unit 11. In the present example, a laser pulse which is redirected by the mirror arrangement 21 is directed in a direction which is opposite the direction of the laser pulse when first emitted into the combustion chamber by the laser device 3. The redirected laser pulse may propagate in a second plane 23-2 which is parallel with a first plane 23-1 in which the laser pulse propagates when being emitted by the gas measurement assembly 1.

The spatial distribution of the gas G and the spatial temperature distribution may be determined in a similar way as described above with reference to FIGS. 3a-b.

A further advantage with the embodiment of FIG. 4 is that also the spatial distribution of the flow rate of the gas G may be determined by means of the present set up. It is however to be noted that the placement of the mirror arrangement may differ, depending on the application. The skilled person would readily contemplate different arrangements for the mirror arrangement in this regard.

The determining of the flow rate along a flow axis 25 transverse to the optical axis will now be described. The present example of determining the flow rate is based on two-dimensional backscattering measurements.

The flow axis 25 is located at a distance d2 from the wall of the combustion chamber 17.

Light or photons backscattered from a redirected laser pulse which propagates in the second plane 23-2 is detected and determined to be backscattered from gas molecules in the second plane 23-2. This can be calculated by determining the first point in time when the laser pulse enters the combustion chamber 17 via the laser device 3 and by determining a second point of time when the backscattered light is detected. Since the width of the combustion chamber 17 is known, it can be determined when the detected backscattered light originates from molecules in the second plane 23-2.

Figure 3B:
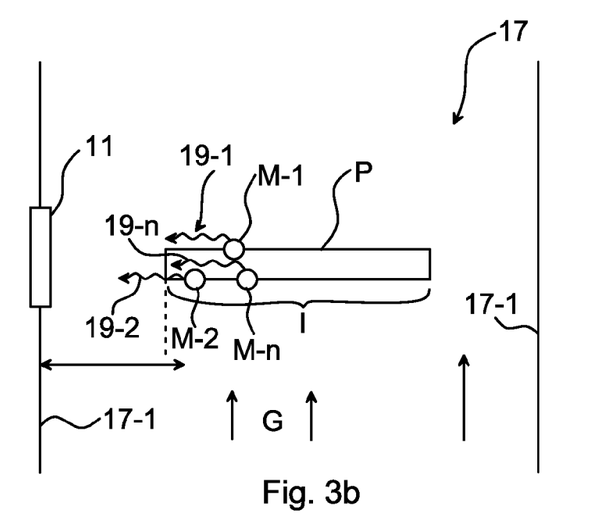

The concentration can then be determined in the vicinity of the intersection of the second plane 23-2 and the flow axis 25 based on the principles described here above with reference to FIG. 3b. The determined concentration of the gas G in the vicinity of the intersection of the second plane 23-2 and the flow axis 25 is then time stamped.

Laser pulses are emitted into the combustion chamber at a rate between e.g. 10 Hz and 500 Hz. Simultaneously as the concentration of the gas G is determined in the vicinity of the intersection of the second plane 23-2 and the flow axis 25, the concentration of the gas G is determined in the vicinity of the intersection of the first plane 23-1 and the flow axis 25 in a similar manner.

When the concentration of the gas is equal to or very similar to the concentration determined in the vicinity of the intersection of the second plane 23-2 and the flow axis 25 this is also time stamped. The flow rate along the flow axis 25 can then be determined by the processing arrangement 7 by determining the difference in time between the measurements of the concentration as determined in the vicinity of the intersection of the second plane 23-2 and the flow axis 25 and the similar measurement results in the vicinity of the intersection of the first plane 23-1 and the flow axis 25.

The mass flow may be determined by multiplying the concentration with the flow rate.

The spatial temperature distribution may be determined in the same manner as described here above with reference to FIGS. 3a-b.

In any of the embodiment presented herein, one or more mirrors may be used for defining a detection plane in the combustion chamber. Such a mirror may be arranged in the same plane as the optical axis O in FIG. 2, on a far end of the combustion chamber inner wall with respect to the laser device.

The gas measurement arrangement described herein may find applications in gas measurements in power plants, and in any similar fields, where gas flow and the determining of the distribution of gas characteristics and/or conditions is of importance.

The skilled person in the art realizes that the present invention by no means is limited to the examples described here above. On the contrary, many modifications and variations are possible within the scope of the appended claims. For instance, the two-dimensional flow rate measurements may be performed by means of two parallel laser device set-ups instead of utilizing a mirror arrangement and one laser device. The time of emission of each parallel laser pulse for each individual laser device then may be used for determining the gas flow. Furthermore, the mirror arrangement may be arranged downstream with respect to the principal plane in which the laser pulse is emitted into the chamber instead of upstream as in the example provided hereabove.

The invention claimed is:

1. A method for determining at least one gas condition at a location in a combustion chamber of a power plant or a combined heat and power plant by means of a laser pulse, the method comprising:
    emitting (S1) the laser pulse into the chamber, determining (S2) a first point of time at which the laser pulse is emitted into the chamber,
    detecting (S3) laser light backscattered by gas molecules at the location in the chamber,
    determining (S4) a second point of time at which the laser light backscattered by the gas molecules is detected,
    determining (S5) the location based on the first point of time, the second point of time, and a pulse length of the laser pulse, and
    determining (S6) the at least one gas condition at the location based on at least one characteristic of the backscattered laser light detected at the second point of time.

2. The method as claimed in claim 1, comprising determining the at least one characteristic.

3. The method as claimed in claim 2, wherein the determining the at least one characteristic involves determining an amount of the backscattered laser light.

4. The method as claimed in claim 2, wherein the determining the at least one characteristic involves determining a spectral property of the backscattered laser light.

5. The method as claimed in claim 1, wherein the detected backscattered laser light is Rayleigh scattered laser light.

6. The method as claimed in claim 1, wherein the detected backscattered laser light is Raman scattered laser light.

7. The method as claimed in claim 1, comprising defining a wavelength of the laser pulse.

8. The method as claimed in claim 1, comprising:
    detecting additional backscattered laser light by gas molecules moving towards the location, from the laser pulse propagating in a second plane different than a first plane in which the laser pulse initially propagated in when emitted into the chamber.

9. The method as claimed in claim 8, comprising:
    determining a concentration of the gas molecules in the second plane, and based on the determining of the at least one gas condition at the location in the first plane, and the determined concentration of the gas molecules in the second plane,
    determining a flow rate of the gas at the location in the first plane.

10. A gas measurement arrangement (1) for determining at least one gas condition at a location in a combustion chamber of a power plant or a combined heat and power plant, the gas measurement system comprising:
    a laser device (3) arranged to emit a laser pulse into the chamber,
    a scattering detector (5) arranged to detect light backscattered by gas molecules at the location in the chamber, and
    a processing arrangement (7) adapted to:
        determine a first point of time at which the laser pulse is emitted into the chamber,
        determine a second point of time at which the backscattered laser light is detected by the scattering detector (5),
        determine the location of the gas condition based on the first point of time, the second point of time and a pulse length of the laser pulse, and
        determine the at least one gas condition at the location based on at least one characteristic of the backscattered light detected at the second point of time.

11. The gas measurement arrangement (1) as claimed in claim 10, wherein the processing arrangement (7) is arranged to determine an amount of the backscattered laser light to thereby determine a concentration of the gas at the location of the at least one gas condition.

12. The gas measurement arrangement (1) as claimed in claim 10, wherein the processing arrangement (7) is arranged to determine a temperature at the location of the gas condition based on spectral characteristics of the backscattered laser light.

13. A combustion system (15) comprising:
a gas measurement arrangement (1) according to claim 10,
a combustion chamber adapted to accommodate gas, the chamber having a enclosing wall with an opening arranged to allow a laser pulse from the laser device (3) to be emitted into the combustion chamber.

14. The combustion system (15) as claimed in claim 13, comprising a window unit (11) arranged in the opening of the chamber, which window unit (11) is arranged to allow a laser pulse from the laser device (3) to be emitted into the chamber, the window unit (11) being arranged to be fed by a gas external to the chamber, which gas external to the chamber has a higher pressure than the gas in the chamber.

15. The method as claimed in claim 3, wherein the determining the at least one characteristic involves determining a spectral property of the backscattered laser light.

16. The method as claimed in claim 2, wherein the detected backscattered laser light is Rayleigh scattered laser light.

17. The method as claimed in claim 2, wherein the detected backscattered laser light is Raman scattered laser light.

18. The method as claimed in claim 3, wherein the detected backscattered laser light is Raman scattered laser light.

19. The method as claimed in claim 4, wherein the detected backscattered laser light is Raman scattered laser light.

20. The method as claimed in claim 2, comprising defining a wavelength of the laser pulse.

\* \* \* \* \*